(12) United States Patent
Kerr

(10) Patent No.: US 7,605,369 B2
(45) Date of Patent: Oct. 20, 2009

(54) ASSESSING RUNWAY VISIBILITY TO AIRBORNE INFRARED VISION DEVICES

(75) Inventor: J. Richard Kerr, West Linn, OR (US)

(73) Assignee: Max-Viz, Inc., Portland, OR (US)

( * ) Notice: Subject to any disclaimer, the term of this patent is extended or adjusted under 35 U.S.C. 154(b) by 0 days.

(21) Appl. No.: 11/970,430

(22) Filed: Jan. 7, 2008

(65) Prior Publication Data

US 2008/0164411 A1     Jul. 10, 2008

Related U.S. Application Data

(60) Provisional application No. 60/883,960, filed on Jan. 8, 2007.

(51) Int. Cl.
*H01L 31/00* (2006.01)
(52) U.S. Cl. .................................... 250/330
(58) Field of Classification Search .................. 250/330
See application file for complete search history.

(56) References Cited

U.S. PATENT DOCUMENTS

| | | | |
|---|---|---|---|
| 4,229,653 A | | 10/1980 | Uthe |
| 4,687,337 A | * | 8/1987 | Stewart et al. ............... 356/437 |
| 6,232,602 B1 | | 5/2001 | Kerr |

OTHER PUBLICATIONS

Vogel et al, Dual-band infrared camera, 2005, Proceedings of SPIE, vol. 5964, pp. 59640S-1-59640S-12.*
Korn et al., A system is more than the sum of its parts—conclusion of DLR's enhaned vision project Advise-Pro, 2006, IEEE, pp. 4B4-1-4B4-8.*
Beier et al., IR measurement and image processing for enhanced vision systems in civil aviation, 2001, Proceedings of SPIE, vol. 4363, pp. 207-218.*
Beier et al., Simulation of infrared detection range at fog conditions for Enhanced Vision Systems in civil aviation, 2004, Aerospace Science and Technology, vol. 8, pp. 63-71.*
Beier et al, Measurement and modelling of infrared imaging system at conditions of reduced visibility (fog) for traffic applications, 1994, Proceedings of SPIE, vol. 2223, pp. 175-186.*
Tiana et al., Multispectral uncooled infrared enhanced-vision system for flight test, 2001, Proceedings of SPIE, vol. 4363, pp. 231-236.*

(Continued)

*Primary Examiner*—Constantine Hannaher
*Assistant Examiner*—Kiho Kim
(74) *Attorney, Agent, or Firm*—Stoel Rives LLP

(57) ABSTRACT

A technique for assessing runway visibility to airborne infrared vision devices (EVS) determines the range performance of airborne infrared EVS sensors at a given destination and in real time by extending the modern RVR philosophy to the infrared spectrum. The technique measures extinction coefficients at the infrared sensor wavelengths of interest through deployment of ground-based infrared transmissometer systems. These infrared extinction coefficients are used with computational algorithms that are analogous to those used at visible wavelengths to determine the respective distances at which the background scene and runway lights are discernible using infrared cameras with appropriate image processing. In this technique, infrared sensors replace the human eye as a basic mechanism of sensing through the atmospheric path. The algorithms also account for the image processing and cockpit display functions, in accordance with the ultimate discernment by the pilot's eye when viewing an appropriate display device.

21 Claims, 1 Drawing Sheet

OTHER PUBLICATIONS

Pawlak, J. and Burnham, D., "Visibility Products from Automated Systems," American Meteorological Society, *First Symposium on Integrated Observing Systems*, Feb. 2-7, 1997, paper J10.6, pp. J28-J32.

* cited by examiner

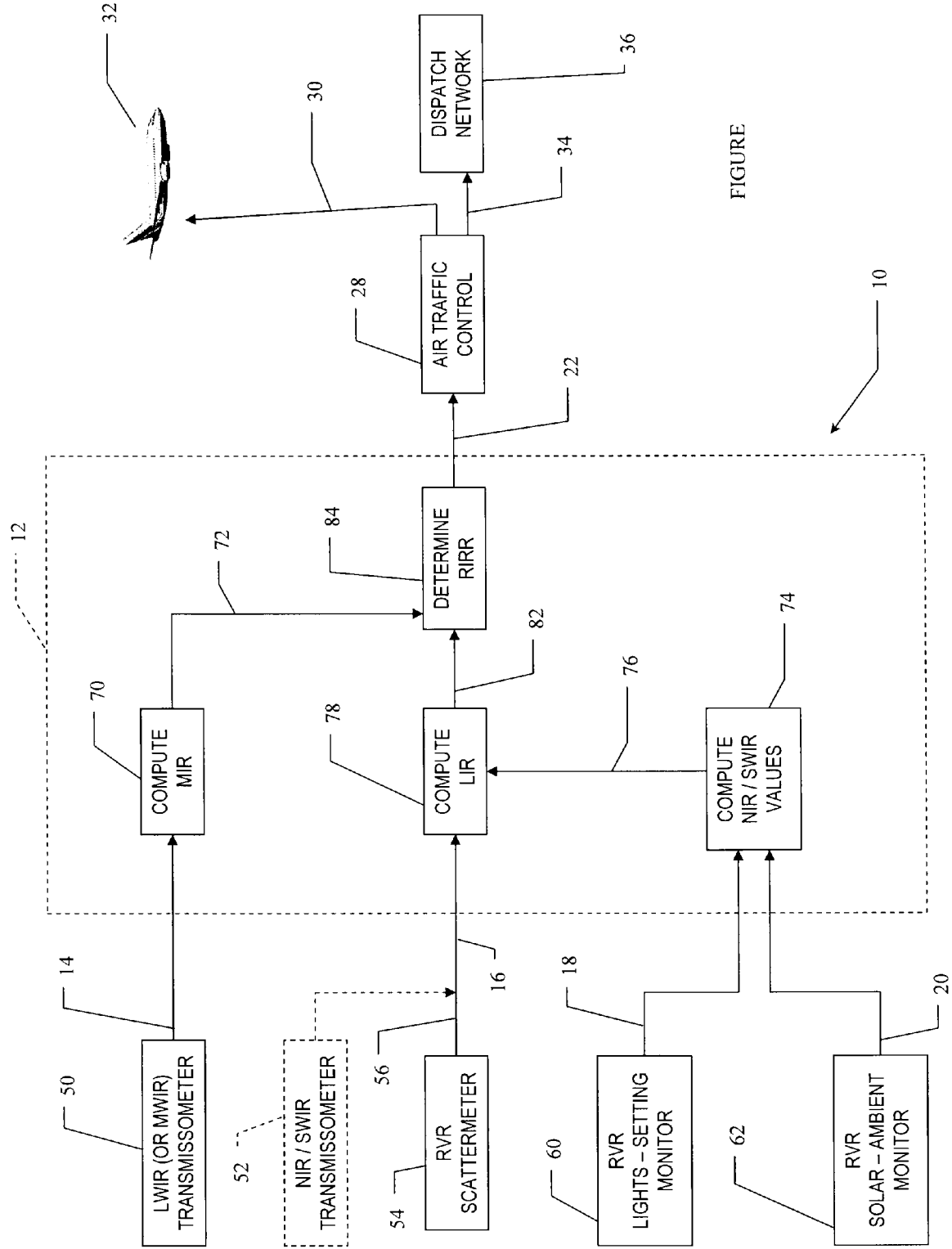
FIGURE

ASSESSING RUNWAY VISIBILITY TO AIRBORNE INFRARED VISION DEVICES

RELATED APPLICATION

This application claims benefit of U.S. Provisional Patent Application No. 60/883,960, filed Jan. 8, 2007.

COPYRIGHT NOTICE

© 2007 Max-Viz, Inc. A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. 37 CFR § 1.71(d).

TECHNICAL FIELD

The present disclosure concerns infrared imaging systems used during periods of inclement weather to enhance visibility for the purpose of safe and efficient air traffic control.

BACKGROUND INFORMATION

Under conditions of diminished visibility, FAA decisions regarding aircraft takeoff and landing operations are based on a parameter known as the Runway Visible Range (RVR), or more simply as the "visibility." RVR is an estimate of how far a pilot can see down a runway and is employed to define operational limits on the use of precision runways. RVR determines what level of equipage is required on both the airfield and any given aircraft to permit takeoff and landing. The RVR is monitored continuously on the ground at each instrumented airfield. In the modern United States implementation, RVR entails the determination of two separate visible ranges, which are $V_K$, or "Koschmieder's visibility," and $V_A$, or "Allard's visibility." $V_K$, or Koschmieder's visibility, which is also known as the Meteorological Optical Range (MOR)=3/σ, is a measure of background-scene contrast (such as runway edges) that depends only upon a parameter known as the atmospheric extinction coefficient σ. $V_A$, or Allard's visibility, is the visibility of runway lighting given by $E_T=(I \exp [-\sigma V_A])/V_A^2$, where I is the luminous intensity at the source. At any given time, the greater of these two visibilities ($V_K$, $V_A$) is reported as the RVR.

An extinction coefficient measures the degree to which a background scene is "extinguished" by weather conditions, notably fog. Fog is a suspension of water droplets, typically from 1 μm-10 μm in diameter. Long wavelength light, greater than 10 μm (long-wave infrared or LWIR), is transmitted through fog, while short wavelength light comparable to or smaller than the sizes of water droplets (e.g., visible spectrum light in the range of 0.4 μm-0.7 μm) is scattered by fog, obstructing the scene in the background. Thus, certain infrared wavebands, having wavelengths longer than the sizes of the water droplets involved, would logically have a significant fog penetration advantage in comparison to visible light. Mid-wave infrared (3 μm-5 μm) (MWIR) imagers may penetrate fog, depending on the distribution of water droplet sizes, but MWIR sensors have the disadvantage of requiring cryogenic cooling of the detector arrays to maintain operational stability. In the LWIR regime, the intensity of heat emitted from objects within the field of view is maximized. This, together with the fog-penetrating property, makes LWIR the most beneficial range for imaging terrain and obstacles.

Short wave (0.7 μm-2.5 μm) infrared (SWIR) or Near Infrared (NIR) imagers yield little, if any, fog penetration advantage. However, runway lights radiate more heat than light, and this heat is primarily in the SWIR (short wave infrared) range. Therefore, a SWIR detector is useful because it enhances the image of runway lights. In addition, in daytime conditions, solar energy is reduced, compared to visible wavelengths of the runway lights. Therefore sensitivity to the lights is increased at all times, and daytime lights-to-solar contrast is higher. NIR/SWIR also has significant advantages under conditions of haze and smog—an increasingly important consideration in a polluted continental environment.

Traditionally, the extinction coefficient has been monitored through use of a two-point, separated source-and-receiver arrangement known as a "transmissometer." A transmissometer fundamentally includes a collimated point source transmitter and a single-element receiver with collecting lens, located some distance away. Fog extinction is inferred by measuring the attenuation between source and receiver under obscured conditions, as compared to the throughput on a clear day.

The art of constructing and calibrating transmissometers is a well-established one. Aspects of transmissometer design and performance include:

(a) automatic monitoring of source intensity, (b) provision of a collimated source beam and narrow field-of-view receiver to minimize reception of forward-scattered light, particularly from multiple scattering in dense fog conditions;

(c) "chopping" and ac-coupling the output if solar energy will otherwise contribute to receiver response;

(d) cleanliness of the sending and receiving optics—freedom from contaminants;

(e) choice of measurement averaging-times, vs patchiness of fog, and wind speeds; and (f) routine re-calibration on clear days.

As the result of a landmark FAA program, the extinction coefficient at modern United States airports is now derived from a basic, single-point measurement performed by a "forward scattermeter" instead of a transmissometer. The scattermeter has an advantage of a large dynamic range.

For many years, there has been great interest in utilizing infrared cameras (also referred to herein as "imagers" or "sensors"), in both night and daytime conditions, as "see-through-fog" enhancements on transport aircraft and ground-based air traffic control systems. A major, specific goal is to permit approach and landing operations at lower minima than would otherwise be permissible for a given level of aircraft and/or airport equipage. To permit FAA dispatch to a destination and, upon arrival in its vicinity, to permit operations below conventional operating minima for that aircraft and airport equipage, it may be necessary to know for certain that the infrared performance is adequate. A dispatch will usually not be permitted without such assurance. More dramatically, any strategy involving final descent with dependence upon eventual runway acquisition with a missed approach (go-around), should infrared penetration turn out to be inadequate, may not be acceptable. Therefore, the infrared performance at the destination runway must be known in "real time" at time of dispatch and at commencement of final approach.

Infrared Enhanced Vision Systems (EVS) have been in use as supplemental equipment on some aircraft since 2003. A basic EVS system aboard an aircraft includes an externally mounted infrared receiver (also referred to as an imager, sensor, or camera), signal processing circuitry, and a cockpit display. The transceiver may be tuned to a narrow range of infrared wavelengths, or it may employ a multi-waveband system. In the most straightforward configuration, the sensor images are utilized in conjunction with a head-up (HUD) and/or head-down display, in order to extend either manual or automatic landing operations. In more advanced configurations, the sensors can be used to derive independent navigation data for multi-thread integration with other subsystems, including Instrument Landing Systems, digital maps, and augmented Global Positioning Satellite technologies. Although recent performance/cost advances in infrared sensors are dramatic, the locational and seasonal variations in fog structure are such that is not possible to know with certainty how much fog penetration airborne infrared EVS provides, and how often.

Current FAA practice defines three standard visibility categories, relating to a standard aircraft approach glideslope:

1. Category I (nominally 2400 foot visibility at 200 foot altitude)
2. Category II (nominally 1200 foot visibility at 100 foot altitude)
3. Category IIIa (nominally 600 foot visibility at 50 foot altitude).

For a given destination, or group of destinations (route structure), it is necessary to know how often the above "certain performance" condition will be satisfied by the infrared sensors. However, unlike the above, this is now a statistical consideration. For example, for a given destination and season, if it could be established, for 90% of Category IIIa visibility conditions, that infrared EVS would provide runway acquisition at a Category I decision height, then the economic value would justify the required investment in the technology.

SUMMARY OF THE DISCLOSURE

The widespread use of airborne infrared imaging equipment could allow flight operations to continue during periods of low visibility if the ground-based infrastructure were also in the infrared regime. EVS equipment is common on aircraft; air traffic control decisions continue, however, to utilize ground-based visible spectrum measurements and the associated RVR rather than infrared spectral measurements, which would accurately indicate the airborne EVS image quality. The economic impact of unnecessarily canceling flight operations for this reason remains unknown, but such impact is anticipated to be significant. Taking full advantage of airborne IR imaging entails re-defining airport safety standards and providing a ground-based IR assessment of fog conditions to judge against the standard.

This disclosure describes a technique that determines the range performance of airborne infrared EVS sensors, at a given destination and in real time by extending the modern RVR philosophy, as described above, to the infrared spectrum. It is well known that the penetration of fog at infrared wavelengths cannot be predicted from visible range data. The technique described measures the extinction coefficient at the infrared sensor wavelength(s) of interest, through the deployment of infrared transmissometer systems. This IR extinction coefficient is used with computational algorithms that are analogous to those used at visible wavelengths to determine the respective distances at which the background scene and runway lights are discernible using infrared cameras with appropriate image processing.

In this technique, infrared sensors replace the human eye as a basic mechanism of sensing through the atmospheric path. The algorithms also account for the image processing and cockpit display functions, in accordance with the ultimate discernment by the pilot's eye when viewing an appropriate display device. An element of the image processing optimizes the detection of lights as well as the clarity of a low contrast background scene, and maps the results to the display.

In parallel with the RVR case, the corresponding fog-penetration visibility range—i.e., runway lights or runway background scene, whichever is greater—is designated as the "Runway Infrared Range" or RIRR. For a single-sensor system, the appropriate RIRR is that corresponding to the particular sensor's waveband. As mentioned above, in advanced systems, the RIRR signal may be used electronically and in computational synergism with other navigation systems. For example, the EVS signal may be used to derive a virtual Instrument Landing System guidance beam through pattern or target recognition or by comparison to a digital map database. In this case, a computer processor's response to the imager output may be more relevant than that of a pilot's eye or a display system, and the RIRR algorithms may require appropriate modification.

The forward scattermeter alternative to transmissometers used for RVR (visible) extinction is not applicable to infrared wavelengths because its principle of operation requires that the wavelength of relevant radiation be shorter than the sizes of scattering particles (fog water droplets). The range of visible wavelengths is roughly 0.3 μm-0.7 μm, while the significant, "polydisperse" fog droplet range is from a few to more than 10 μm in diameter; this satisfies the scattermeter criterion for the visible case. Conversely, these droplets are comparable to or smaller than the longer infrared wavelengths of interest; this is particularly true for MWIR and LWIR. This wavelength-particle size relationship is the reason for a "fog-penetrating advantage" in the infrared, particularly LWIR. However, it also precludes calibration of an infrared extinction measurement utilizing a single-point, single-angle forward scattering device. Restated from the standpoint of scattering physics, the scattermeter operates under the principle of separation of geometrical and diffraction optics effects respectively, and this is not possible for particle/wavelength size ratios on the order of unity or less.

The RIRR extinction coefficients are, therefore, measured using infrared transmissometers, analogous to the classical RVR case. Returning to the use of transmissometers would then be acceptable given sufficient economic justification in the context of low-visibility flight operations. Ground-based infrared transmissometers are not commercially available, but are custom-built as needed. For instance, U.S. Pat. No. 4,229,653 pertains to the use of a single-wavelength IR transmissometer in measuring the mass concentration of particulates emitted from a source of air pollution. The present disclosure proposes that IR transmissometers be used in a different application and environment.

The standard assumption that a horizontal-path transmissometer adequately represents a slant-path aircraft view to the runway is the same as for the visible RVR case. In the event that this assumption is called into question for infrared wavebands, available static-test facilities with towers for slant-paths can be used to establish any required biasing on the horizontal data.

Each transmissometer configuration preferably includes separate transmitter and receiver components, or a combined transceiver with infrared retroreflectors. The retroreflectors may be passive (unpowered), placed non-collinearly with respect to the transceiver, and thereby require the transceiver signal to be sequentially steered to each retroreflector, or active, placed in the transceiver line-of-sight with sequential selection via a built-in shutter. In either case, through provision of progressively greater reflection cross-sections as distances increase, a very large equivalent dynamic range may be achieved. In the retroreflector configuration, the source and detector can be directly coupled to achieve instrument calibration/monitoring at any chosen interval. The use of retroreflectors also mitigates forward-scattering errors in the measurement.

A preferred embodiment of the system disclosed is to be utilized in conjunction with a dual-infrared EVS sensor approach described in U.S. Pat. No. 6,232,602, though in general, the RIRR system described is compatible with various EVS configurations: dual sensors, single waveband sensors, or a combination of the two. RIRR determination parallels the RVR case in that the two component visibilities—background and lights—relate to two separate imagers operating within different wavebands. These different wavebands are referred to as background scene waveband for the background visibility component and runway light waveband for the lights visibility component. When used with a dual-IR EVS approach, LWIR or MWIR detectors are used for the background/runway scene, while a NIR/SWIR detector is used for the runway lights. In simpler infrared EVS systems, a single imager may be used instead of the dual-sensor configuration.

There are at least three options for a single-imager EVS: the first option entails use of a LWIR camera for background/runway scene only (the lights will be visible insofar as their outer shells are warm). Alternatively, this role may be fulfilled by a MWIR imager. The second option entails a NIR/SWIR camera for lights-enhancement only. The third option combines SWIR/MWIR (dual-waveband) sensitivity in a single imaging sensor. In this approach, both the background and lights are viewed by a common focal plane array, and their respective signals are superimposed at the array output. A difficulty with this approach is that there is a large dynamic range required to process both the background image signals along with the much larger lights/solar signals.

In the practical case, a diode laser or emitter is utilized as the source at some intermediate LWIR wavelength, such as 10 μm. This source affords a reasonable measure of extinction over the LWIR band, and because of its high intensity, permits the use of an inexpensive photodetector. The receiver unit may utilize a microbolometer, a thermoelectrically cooled HgCdTe detector, or other LWIR detector with adequate sensitivity and linearity when matched with the source and expected extinction range of interest.

If a more elaborate representation of the imager spectral response is desired, the source can be a heated element. The source/detector combination emulates the imager response combined with the LWIR spectrum of a cool, ambient background; this can be achieved with appropriate spectral weighting (filtering). Single-element photodiode detectors sensitive in the SWIR waveband are widely available using, for example, InGaAs or HgCdTe technology. For the NIR, silicon photodetectors are suitable. Because of the significant daytime solar content at these wavelengths, an optimal transmissometer uses a pulsed source and an ac-coupled receiver.

The dynamic range of the infrared transmissometer is determined by the linear range of detector operation between saturation at the high end and noise at the low end. This assumes that the source intensity and optical parameters are such that the receiver signal in clear-air conditions is near its saturation level. The RVRs of interest are roughly as follows:
Category I: 800 meters
Category II: 400 meters
Category III: 200 to 50 meters or less.

The corresponding range of extinction coefficients is such that receiver signals may span orders of magnitude. This is also true at infrared wavelengths. For that reason, two or more sets of transmitter/receiver baseline separations may be desirable.

Standard practice with an RVR transmissometer is to trim the calibration on sensibly "clear" days. Because the period between such scenarios may be unpredictable, it is also necessary to monitor and control the source intensity. This is readily achieved through the use of an auxiliary detector mounted within the transmitter with off-axis geometry, or a beamsplitter situated to view the source in an attenuated manner. This auxiliary detector can be used to control source intensity through a simple feedback circuit. Obstructions on the optics or reflectors tend to cause errors on the conservative side, i.e., high extinction value.

A set of algorithms for calculating the RIRR from the extinction values extends the RVR philosophy to the infrared spectrum and employs calculations analogous to those used at visible wavelengths to determine, from the extinction coefficients supplied by the infrared transmissometers, at what distance the background scene and runway are discernable to the airborne EVS. Thus, calculating RIRR entails determining two infrared "visibility" ranges, with the greater of the two representing the desired RIRR in any given scenario. The calculation of either range entails the basic measure of infrared extinction at the appropriate wavelength. A Meteorological Infrared Range (MIR) is the counterpart to the MOR, and a Lights Infrared Range (LIR) is the IR counterpart to the Allard's visibility range, in which the definitions have the IR extinction values substituted for the visible extinction values. With these substitutions, $$MIR=3/\sigma_{IR},$$

where $\sigma_{IR}$ is the measured infrared extinction at LWIR (or MWIR). The LIR is given by $$S_T=[I_{IR} \exp[-\sigma_{IR}(LIR)]]/(LIR)^2,$$

where ($S_T$) is the input signal threshold at the imager, $I_{IR}$ is the infrared intensity at the light source, and $\sigma_{IR}$ is the measured infrared extinction, both of $I_{IR}$ and $\sigma_{IR}$ taken at NIR/SWIR wavelengths of interest. The value of $I_{IR}$ can be inferred from the normal RVR monitoring of the lights setting (I), along with their known output spectral distributions at each setting.

As in the visible case, in the daytime, if a particular imager has significant solar response, the value of $S_T$ is also a function of NIR/SWIR background solar level, $B_{IR}$. This may be calculated from solar radiometric data, using the standard-imager spectral response and the normal RVR monitoring of visible background solar level, B. Alternatively, the solar background level may be monitored directly at the NIR/SWIR wavelength of interest. Given the monitored values of $\sigma_{IR}$, $I_{IR}$ and $B_{IR}$, and an algorithm that relates $S_T$ to the given $B_{IR}$, the above equation is solved for LIR. For this infrared case, where the eye is not the primary sensor, physical units (based on Watts/sr and irradiance) are used for $I_{IR}$ and $S_T$ respectively.

By placing RIRR instrumentation at a busy airport (such as a hub), and letting it record data through a season of fog, the potential user can establish the number of times for which EVS would have permitted dispatch and landing approach in otherwise inclement conditions. The accuracy must be sufficient to provide confidence in the data, but the instrumentation does not require FAA certification, and the requirement for actual flight tests is avoided.

Additional aspects and advantages will be apparent from the following detailed description of preferred embodiments, which proceeds with reference to the accompanying drawings.

BRIEF DESCRIPTION OF THE DRAWINGS

The FIGURE is a block diagram of a preferred embodiment of a system for computing runway infrared range (RIRR).

DETAILED DESCRIPTION OF PREFERRED EMBODIMENTS

The FIGURE is a block diagram of a preferred embodiment of a system 10 for computing runway infrared range (RIRR) or infrared visibility. System 10 includes a runway infrared range computer system 12, which is indicated by a dashed line box in the FIGURE. A set of four input signals representing, for a destination airport, an LWIR (or MWIR) background scene extinction coefficient signal 14, a NIR/SWIR runway lights extinction coefficient signal 16, an RVR system lights intensity-setting signal 18, and an RVR system solar-ambient level signal 20 are applied to processors of RIRR computer system 12 for computation of a value of an RIRR signal 22. The RIRR signal value describes the local IR "visibility" range conditions presented to aircraft equipped with EVS. Air traffic control 28 receives RIRR signal 22 and uses its value to transmit by conventional communication links an EVS approach and landing signal 30 to an EVS-equipped transport aircraft 32 to control its flight operation and dispatch signals 34 to a dispatched network 36 to control dispatch of aircraft 32 to the airport as a destination.

More specifically, a transmissometer 50 for a background scene produces at its output a value of extinction coefficient signal 14 for the LWIR (or MWIR) wavelength of the relevant camera. A separate transmissometer 52 (shown in dashed lines) for runway lights produces at its output a value of NIR/SWIR runway lights extinction coefficient signal 16 at the wavelength of interest. In the alternative, as an approximation, a standard RVR scattermeter 54 may be used with its visible-extinction output signal 56 functioning as NIR/SWIR extinction coefficient signal 16. A standard RVR system lights-setting monitor 60 provided for the setting of the lights intensity is used to derive the corresponding lights intensity-setting signal 18. Similarly, a standard RVR system monitor 62 provided for determining a solar-ambient level produces solar-ambient level signal 20. Alternatively, solar-ambient monitor 62 may operate directly at the NIR/SWIR wavelength of interest.

Signals 14, 16, 18, and 20 are delivered to processors in RIRR computer system 12. A processor 70 derives from background scene extinction coefficient signal 14 a Meteorological Infrared Range value 72 using LWIR (or MWIR) standard-camera parameters, display parameters, and pilots' eye parameters. A processor 74 converts the lights setting provided by lights intensity-setting 18 and the solar-ambient level provided by solar-ambient level signal 20 to values 76 for the NIR/SWIR wavelength of interest. Runway lights extinction coefficient signal 16 and solar-ambient and lights-setting values 76 are used in processor 78 to derive a Lights Infrared Range value 82, using NIR/SWIR standard-camera parameters with display and pilots' eye parameters. A final processor 84 assigns the greater of values 72 and 82 as RIRR value 22, which is then used by air traffic control 28 to control EVS approach and landing as well as dispatch to the destination airport.

Skilled persons will appreciate that aircraft equipped with an RIRR computer system may receive extinction values directly from ground-based transmissometers and calculate the IR visibility range, i.e., RIRR value, on-board.

It will be obvious to those having skill in the art that many changes may be made to the details of the above-described embodiments without departing from the underlying principles of the invention. The scope of the present invention should, therefore, be determined only by the following claims.

The invention claimed is:

1. A method of permitting dispatch of pilot-operated, enhanced vision system (EVS)-equipped transport aircraft to a destination and, upon approach of the aircraft to the destination, permitting operations below conventional operating minima for the EVS-equipped transport aircraft and destination equipage, the EVS including EVS infrared sensors that operate at wavelengths and are characterized by range performance, and the destination characterized by contrast within a background scene in a background scene waveband and intensity of aircraft runway lights in a runway light waveband, comprising:

using a ground-based infrared visibility measurement system to provide EVS range performance information that includes first and second infrared visibility levels at wavelengths of the EVS infrared sensors with which the transport aircraft is equipped, the first infrared visibility level corresponding to the contrast within the background scene in the background scene waveband and the second infrared visibility level corresponding to the intensity of the aircraft runway lights in the runway light waveband;

determining atmospheric extinction coefficients at the background scene waveband and the runway light waveband; and predicting for the EVS infrared sensors an EVS range of distances at which the background scene and aircraft runway lights at the destination are discernible by the EVS infrared sensors, the EVS range of distances determined by processing of the EVS range performance information and the atmospheric extinction coefficients at the background scene and runway light wavebands, thereby to provide a predicted EVS range of distances that preclude or minimize a chance of a missed-approach maneuver by the transport aircraft dispatched to or approaching the destination.

2. The method of claim 1, in which the EVS includes an EVS imager and the ground-based infrared visibility measurement system comprises an infrared transmissometer that is operationally wavelength-matched to the EVS imager.

3. The method of claim 2, in which the background scene waveband includes a long wavelength infrared (LWIR) waveband, in which the EVS imager operates within the LWIR waveband to image terrain and obstacles in the background scene, and in which the infrared transmissometer includes a LWIR source operating within a waveband that is compatible with the LWIR waveband.

4. The method of claim 2, in which the background scene waveband includes a mid-wavelength infrared (MWIR) waveband, in which the EVS imager operates within the MWIR waveband to image terrain and obstacles in the background scene, and in which the infrared transmissometer includes a MWIR source operating within a waveband that is compatible with the MWIR waveband.

5. The method of claim 2, in which the runway light waveband includes a near infrared/short wavelength infrared (NIR/SWIR) waveband, in which the EVS imager operates within the NIR/SWIR waveband to enhance and detect the aircraft runway lights, and in which the infrared transmissometer includes a NIR/SWIR source operating within a waveband that is compatible with the NIR/SWIR waveband.

6. The method of claim 2, in which the infrared transmissometer includes a light source operating within a waveband and a receiver spanning the same waveband as that of the light source.

7. The method of claim 6, in which the receiver is of either a dual-waveband device type or a single wavelength device type.

8. The method of claim 6, in which the receiver includes a light collecting lens and a detector.

9. The method of claim 1, in which the processing of the EVS range performance information and the atmospheric extinction coefficients comprises:
    deriving in part from the atmospheric extinction coefficients at the background scene and runway light wavebands respective meteorological infrared range and lights infrared range values; and
    assigning to the greater of the meteorological infrared range and lights infrared range values a Runway Infrared Range (RIRR) value, the RIRR value indicating a pilot's ability to see down a runway and providing a basis for an air traffic controller to control approach or dispatch of the EVS-equipped transport aircraft to the destination.

10. The method of claim 9, in which the background scene and runway light wavebands include respective LWIR and NIR/SWIR wavebands, and in which the deriving of the meteorological infrared range and lights infrared range values comprises:
    calculating a first intermediate range that is inversely proportional to the atmospheric extinction coefficient at the background scene LWIR waveband;
    calculating a second intermediate range that is a function of the atmospheric extinction coefficient at the runway light NIR/SWIR waveband; and
    assigning as the RIRR value the greater of the calculated first and second intermediate ranges.

11. The method of claim 10, further comprising using the RIRR value as an indicator of the severity of weather conditions in obscuring ground visibility at the destination, thereby to establish an air traffic control standard against which an EVS-equipped aircraft is evaluated and qualified for landing in existing fog conditions.

12. The method of claim 9, in which the background scene and runway light wavebands include respective MWIR and NIR/SWIR wavebands, and in which the deriving of the meteorological infrared range and lights infrared range values comprises:
    calculating a first intermediate range that is inversely proportional to the atmospheric extinction coefficient at the background scene MWIR waveband;
    calculating a second intermediate range that is a function of the atmospheric extinction coefficient at the runway light NIR/SWIR waveband; and
    assigning as the RIRR value the greater of the calculated first and second intermediate ranges.

13. A ground-based infrared visibility measurement system for monitoring ground level fog extinction in the vicinity of an airport runway, the airport runway vicinity characterized by contrast within a background scene in a background scene waveband and intensity of aircraft runway lights in a runway light waveband, and the system predicting the quality of an image of the airport runway as produced by enhanced vision system (EVS) infrared sensors of EVS equipment of a transport aircraft approaching the airport runway, comprising:
    first and second infrared light sources cooperating with a receiver to provide EVS range performance information that includes first and second infrared visibility levels at wavelengths of operation of the EVS infrared sensors with which the transport aircraft is equipped, the receiver wavelength-matched to the wavelengths of operation of the first and second infrared light sources;
    the first infrared light source and receiver cooperating to provide the first infrared visibility level to which the contrast within the background scene in the background scene waveband corresponds and from which an atmospheric extinction coefficient at the background scene waveband can be determined;
    the second infrared light source and receiver cooperating to provide the second infrared visibility level to which the intensity of the runway lights in the runway light waveband corresponds and from which an atmospheric extinction coefficient at the runway light waveband can be determined; and
    a signal processor implemented with an algorithm that processes the EVS range performance information and the atmospheric extinction coefficients at the background scene and runway light wavebands to predict, for the EVS infrared sensors, an EVS range of distances that preclude or minimize a chance of missed-approach maneuver by the transport aircraft dispatched to or approaching the destination.

14. The system of claim 13, in which the first infrared light source is part of a ground-based LWIR or MWIR transmissometer.

15. The system of claim 13, in which the second infrared light source is part of a ground-based NIR/SWIR transmissometer.

16. The system of claim 13, in which the receiver is of either a dual-waveband device type or a single wavelength device type.

17. The system of claim 13, in which the receiver includes a light collecting lens and a detector.

18. The system of claim 13, in which the signal processor implemented with an algorithm processes the atmospheric extinction coefficients at the background scene and runway light wavebands to derive respective meteorological infrared range and lights infrared range values and assigns to the greater of the meteorological infrared range and lights infrared range values a RIRR value that indicates a pilot's ability to see down a runway and provides a basis for an air traffic controller to decide whether to control approach or dispatch of the EVS-equipped transport aircraft to the destination.

19. The system of claim 18, in which the background scene and runway light wavebands include respective LWIR and NIR/SWIR wavebands, and in which the processing to derive the meteorological infrared range and lights infrared range values includes calculating a first intermediate range that is inversely proportional to the atmospheric extinction coefficient at the background scene LWIR waveband and a second intermediate range that is a function of the atmospheric extinction coefficient at the runway light NIR/SWIR waveband, and assigning as the RIRR value the greater of the calculated first and second intermediate ranges.

20. The system of claim 18, in which the RIRR value further indicates the severity of weather conditions in obscuring ground visibility at the destination, thereby to establish an air traffic control standard against which an EVS-equipped aircraft is evaluated and qualified for landing in existing fog conditions.

21. The system of claim 18, in which the background scene and runway light wavebands include respective MWIR and NIR/SWIR wavebands, and in which the processing to derive the meteorological infrared range and lights infrared range values includes calculating a first intermediate range that is inversely proportional to the atmospheric extinction coefficient at the background scene MWIR waveband and a second intermediate range that is a function of the atmospheric extinction coefficient at the runway light NIR/SWIR waveband, and assigning as the RIRR value the greater of the calculated first and second intermediate ranges.

* * * * *